(12) United States Patent
Zhang et al.

(10) Patent No.: US 12,182,484 B2
(45) Date of Patent: Dec. 31, 2024

(54) INDIVIDUAL IMPEDANCE-BASED RADIO-FREQUENCY HEATING TEMPERATURE FIELD PREDICTION METHOD AND SYSTEM

(71) Applicant: MAGI COMPANY LTD, Shanghai (CN)

(72) Inventors: Aili Zhang, Shanghai (CN); Fangyu Qin, Shanghai (CN); Kangwei Zhang, Shanghai (CN); Xuemin Xu, Shanghai (CN)

(73) Assignee: MAGI COMPANY LTD, Shanghai (CN)

( * ) Notice: Subject to any disclaimer, the term of this patent is extended or adjusted under 35 U.S.C. 154(b) by 1015 days.

(21) Appl. No.: 17/258,129

(22) PCT Filed: Jun. 28, 2019

(86) PCT No.: PCT/CN2019/093702
§ 371 (c)(1),
(2) Date: Apr. 1, 2021

(87) PCT Pub. No.: WO2020/007245
PCT Pub. Date: Jan. 9, 2020

(65) Prior Publication Data
US 2021/0232736 A1   Jul. 29, 2021

(30) Foreign Application Priority Data
Jul. 5, 2018   (CN) .......................... 201810730963.5

(51) Int. Cl.
*G06F 30/23* (2020.01)
*A61B 18/00* (2006.01)
(Continued)

(52) U.S. Cl.
CPC ..... *G06F 30/23* (2020.01); *A61B 2018/00041* (2013.01); *A61B 2018/00577* (2013.01);
(Continued)

(58) Field of Classification Search
None
See application file for complete search history.

(56) References Cited

U.S. PATENT DOCUMENTS 6,575,969 B1   6/2003   Rittman et al.
7,702,495 B2 *   4/2010   Humphries ............ G09B 23/30
600/416
(Continued)

FOREIGN PATENT DOCUMENTS

CN   1631327 A   6/2005
CN   106073890 A   11/2016
(Continued)

OTHER PUBLICATIONS

D. Haemmerich, "Mathematical modeling of impedance controlled radiofrequency tumor ablation and ex-vivo validation," 2010 Annual International Conference of the IEEE Engineering in Medicine and Biology, Buenos Aires, Argentina, 2010, pp. 1605-1608 (Year: 2010).*

(Continued)

*Primary Examiner* — Akash Saxena
(74) *Attorney, Agent, or Firm* — HSML P.C.

(57) ABSTRACT

The present application relates to the field of biomedical engineering. Disclosed are an individual impedance-based radio-frequency heating temperature field prediction method and system which greatly improve the rate and accuracy of temperature distribution prediction. The method of the present application comprises: creating a first region; obtaining a position of an ablation needle, and with the ablation needle as a center, creating a second region in the first region;

(Continued)

keeping the electrical conductivity within the second region constant, and adjusting the electrical conductivity in the first region such that impedance between the ablation needle and an earth pole is consistent with real individual impedance actually measured by a treatment system; performing mesh division on a combination of the first region and the second region and performing coupling computation using a radio-frequency field model and a biological heat transfer model to obtain temperature field time-space information.

10 Claims, 4 Drawing Sheets

(51) Int. Cl.
    *A61B 34/10*     (2016.01)
    *G06F 119/08*     (2020.01)

(52) U.S. Cl.
    CPC ..... *A61B 2018/00755* (2013.01); *A61B 34/10* (2016.02); *A61B 2034/104* (2016.02); *A61B 2034/105* (2016.02); *G06F 2119/08* (2020.01)

(56) References Cited

U.S. PATENT DOCUMENTS

| | | | | |
|---|---|---|---|---|
| 9,198,733 | B2* | 12/2015 | Neal, II | A61B 18/12 |
| 9,846,765 | B2* | 12/2017 | Audigier | G09B 23/30 |
| 11,396,642 | B2* | 7/2022 | Xu | C07K 14/47 |
| 11,944,384 | B2* | 4/2024 | Xu | A61B 34/10 |
| 2007/0043345 | A1* | 2/2007 | Davalos | A61B 18/1233 |
| | | | | 606/41 |
| 2009/0221999 | A1* | 9/2009 | Shahidi | A61B 34/10 |
| | | | | 128/898 |
| 2011/0015628 | A1* | 1/2011 | Dalal | A61B 18/1477 |
| | | | | 606/34 |
| 2011/0196385 | A1* | 8/2011 | Altrogge | A61B 34/10 |
| | | | | 703/2 |
| 2014/0296842 | A1 | 10/2014 | Mansi et al. | |
| 2015/0366613 | A1 | 12/2015 | Crump et al. | |
| 2018/0020926 | A1 | 1/2018 | Stang et al. | |
| 2018/0168534 | A1* | 6/2018 | Desponds | A61B 6/40 |
| 2020/0367971 | A1* | 11/2020 | Xu | A61B 34/10 |
| 2021/0232736 | A1* | 7/2021 | Zhang | G16H 50/50 |
| 2022/0117668 | A1* | 4/2022 | Qin | A61B 34/20 |

FOREIGN PATENT DOCUMENTS

| | | |
|---|---|---|
| CN | 107049476 A | 8/2017 |
| CN | 107526928 A | 12/2017 |
| CN | 107578820 A | 1/2018 |
| CN | 108830017 A | 11/2018 |

OTHER PUBLICATIONS

R Padma Suvarna et al, A simple technique for a.c. conductivity measurements , Bull. Mater. Sci., vol. 25, No. 7, Dec. 2002, pp. 647-651. © Indian Academy of Sciences (Year: 2002).*

Wikipedia definition Electrical resistance and conductance, Downloaded Jun. 7, 2024, p. 11 (Year: 2024).*

K. Frank, H. Lindenborn and D. Dahlhaus, "Numerical and experimental characterization of radiofrequency ablation in perfused kidneys," 2012 Annual International Conference of the IEEE Engineering in Medicine and Biology Society, San Diego, CA, USA, 2012, pp. 5707-5711, doi: 10.1109/EMBC.2012.6347291. (Year: 2012).*

F. Qin, K. Zhang, J. Zou, J. Sun, A. Zhang and L. X. Xu, "A New Model for RF Ablation Planning in Clinic," 2018 40th Annual International Conference of the IEEE Engineering in Medicine and Biology Society (EMBC), Honolulu, HI, USA, 2018, pp. 3232-3235, doi: 10.1109/EMBC.2018.8512926. (Jul. 18-21, 2018) (Year: 2018).*

International Search Report and Written Opinion issued in PCT/CN2019/093702, mailed Sep. 30, 2019, with English translation.

Office Action (with search report) issued in Chinese Application No. 201810730963.5, dated Jun. 23, 2021, with English translation.

Sun et al., "Simulation Analysis of Microwave Ablation based on Dynamic Biological Tissue properties", Journal of Biomedical Engineering Research, 35(1), 2016, pp. 12-17, with English Abstract.

Wang et al., "Parametric Sensitivity Analysis of Simulation Model for Temperature-Controlled Radiofrequency Ablation Temperature Field", China Academic Journal Electronic Publishing House, vol. 32 No. 9, 2017.

Zurbuchen et al., "Determination of the temperature-dependent electric conductivity of liver tissue ex vivo and in vivo: Importance for therapy planning for the radiofrequency ablation of liver tumours", International Journal of Hyperthermia, 26:1, 26-33, Published online: Jan. 25, 2010.

Possebon et al., "A piecewise function of resistivity of liver: determining parameters with finite element analysis of radiofrequency ablation", Med Biol Eng Comput (2018) 56:385-394, Published online: Aug. 2, 2017.

* cited by examiner

INDIVIDUAL IMPEDANCE-BASED RADIO-FREQUENCY HEATING TEMPERATURE FIELD PREDICTION METHOD AND SYSTEM

TECHNICAL FIELD

The present application relates to the field of biomedical engineering, in particular to individual impedance-based radio-frequency heating temperature field prediction technology.

BACKGROUND

With the development of modern imaging technology and computerized surgical guidance technology, minimally invasive thermal ablation technology has received extensive attention in tumor treatment. Percutaneous radio frequency ablation (RFA) is a thermotherapy alternative to surgical resection of liver cancer. During RFA treatment, when ions and polar molecules oscillate in an alternating magnetic field, high-frequency alternating current will cause friction heating, which will cause the temperature to rise above 60° C., causing instantaneous denaturation of proteins and cell nucleus, and direct necrosis or apoptosis of tumor cells.

The key to achieve effective RFA treatment is to precisely control the size and shape of an ablation region (thermocoagulation region) to avoid residual tumor tissue and collateral damage to normal tissues. Mathematical modeling provides an effective method to predict the temperature field and the corresponding tissue damage range, which is of great significance for formulating more precise treatment plans. Researchers have been committed to improve the accuracy and rate of simulation.

However, inventors of the present application found that in the process of a simulating RFA treatment, computation results of the existing modeling methods often deviate greatly from actual situation.

SUMMARY OF THE INVENTION

The purpose of the present application is to provide an individual impedance-based radio-frequency heating temperature field prediction method and system, which greatly improve the accuracy temperature distribution prediction.

In order to solve the above problems, the present application discloses an individual impedance-based radio-frequency heating temperature field prediction method, comprising:

creating a first region;

obtaining a position of an ablation needle, and with the ablation needle as a center, creating a second region in the first region;

keeping the electrical conductivity within the second region constant, and adjusting the electrical conductivity in the first region such that an impedance between the ablation needle and an earth pole is consistent with a real individual impedance actually measured by a treatment system; and performing mesh division on a combination of the first region and the second region and performing coupling computation using a radio-frequency field model and a biological heat transfer model to obtain temperature field time-space information.

In a preferred embodiment, the first region is an elliptic cylinder, and the second region is a cylinder.

In a preferred embodiment, the second region covers an ablation range of the ablation needle.

In a preferred embodiment, the ablation needle is a unipolar, or bipolar, and multipolar ablation needle.

In a preferred embodiment, the ablation needle is inserted vertically into the first region.

In a preferred embodiment, the radio-frequency field model adopts a quasi-electrostatic field model.

In a preferred embodiment, the biological heat transfer model adopts a Pennes biological heat transfer model.

In a preferred embodiment, in the step of performing coupling computation using a radio-frequency field model and a biological heat transfer model, a finite element method is used for numerical computation.

The application also discloses an individual impedance-based radio-frequency heating temperature field prediction system, comprising:

a first region creating unit, configured to create a first region;

a second region creating unit, configured to obtain a position of an ablation needle, and with the ablation needle as a center, create a second region in the first region;

an electrical conductivity setting unit, configured to keep the electrical conductivity within the second region constant, and adjust the electrical conductivity in the first region such that an impedance between the ablation needle and an earth pole is consistent with a real individual impedance actually measured by a treatment system; and a computation unit, configured to perform mesh division on a combination of the first region and the second region and perform coupling computation using a radio-frequency field model and a biological heat transfer model to obtain temperature field time-space information.

The application also discloses an individual impedance-based radio-frequency heating temperature field prediction system, comprising:

a memory for storing computer executable instructions; and a processor, configured to implement the steps of the above-described method when executing the computer executable instructions.

The present application also discloses a computer readable storage medium that stores computer executable instructions which are executed by a processor to implement the steps of the above-described method.

In the embodiments of the present application, by cleverly designing a simple geometric structure and fully considering the differences of individual impedances, the rate and accuracy of temperature distribution prediction are greatly improved, which will facilitate the formulation of more accurate clinical radio-frequency treatment plans, intraoperative monitoring of the treatment process, and prediction and evaluation of treatment results.

Furthermore, setting the first region as an elliptic cylinder and the second region as a cylinder greatly simplifies the computation process and speeds up the computation speed on the premise that the computation accuracy requirements can be met.

A large number of technical features are described in the specification of the present application, and are distributed in various technical solutions. If combinations of all possible technical features (i.e., technical solutions) of the present application are listed, the description may be made too long. In order to avoid this problem, the various technical features disclosed in the above summary of the present application, the technical features disclosed in the various embodiments and examples below, and the various technical features disclosed in the drawings can be freely combined with each other to constitute various new technical solutions (all of which are considered to have been described in this specification), unless a combination of such technical features is not technically feasible. For example, feature A+B+C is disclosed in one example, and feature A+B+D+E is disclosed in another example, while features C and D are equivalent technical means that perform the same function, and technically only choose one, not to adopt at the same time. Feature E can be combined with feature C technically. Then, the A+B+C+D scheme should not be regarded as already recorded because of the technical infeasibility, and A+B+C+E scheme should be considered as already documented.

DETAILED DESCRIPTION

Figure 1:
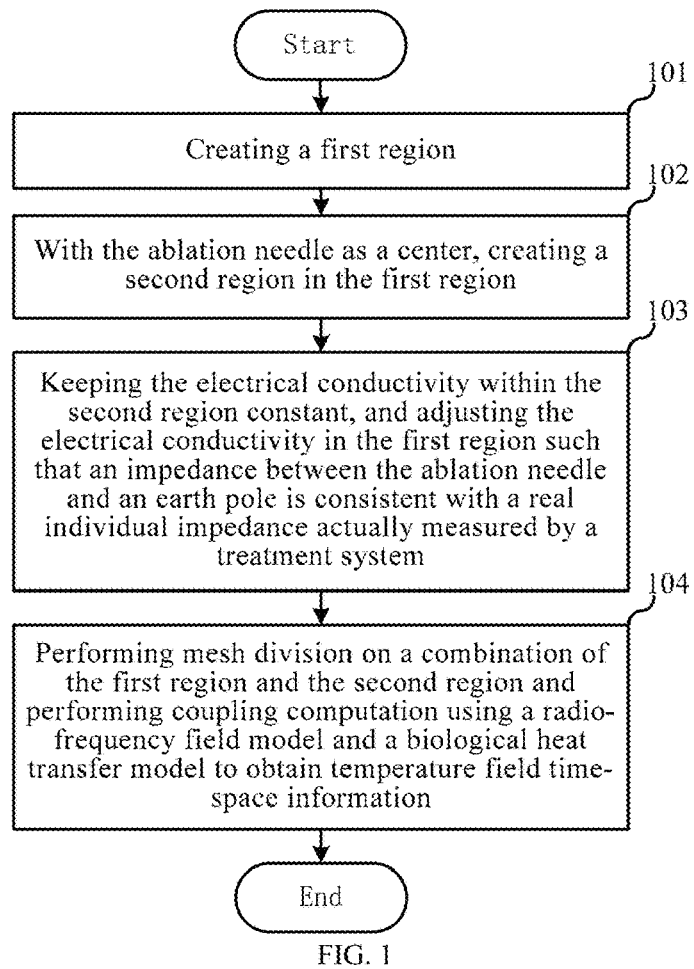
FIG. 1 is a schematic flowchart of an individual impedance-based radio-frequency heating temperature field prediction method in a first embodiment of the present application.

In the following description, numerous technical details are set forth in order to provide the reader with a better understanding of the present application. However, those skilled in the art can understand that the technical solutions claimed in the present application can be implemented without these technical details and various changes and modifications based on the following embodiments.

The following is a summary of some of the innovations of the present application:

The inventors of the present application found that in the process of simulating RFA treatment, the existing modeling method usually does not consider individual differences between patients, and sets the electrical conductivity of a tissue to a constant value, or sets the position of a negative electrode at the bottom of a liver. The simulating process only considers the electrical conductivity of the liver. However, in actual clinical operations, the position of the negative electrode is often attached to the hip or back of the individual. Therefore, placing the negative electrode at the bottom of the liver or the simulation method that does not consider the differences in individual electrical properties will cause great deviations. In clinical RFA operations, the individual impedance is often recorded and used to determine whether the tissue is carbonized during the radio-frequency heating process. At the same time, the impedance reflects the impedance between the positive and negative electrodes, including the impedance of the liver and the impedance of the individual torso. Due to the differences between individuals and tissues, the impedance between different individuals is not the same, which has a great impact on the study of radio-frequency energy distribution in the liver tissue. Therefore, based on the above information, the inventors innovatively proposed an individual impedance-based radio-frequency heating temperature field prediction method, and verified the accuracy of the model with experimental measurement results.

The present application first creates a large geometry based on the size of a human body (that is, the first region), which represents the torso tissue of the object to be ablated (such as the human or animal body), and then uses an ablation needle as the center to create a small geometry (that is, the second region) in the large geometry, which represents the tissue of the target ablation region. The electrical conductivity of the small internal geometry remains constant (for example, it is uniformly set to the tissue electrical conductivity used in the literature), and the electrical conductivity of the large external geometry is adjusted so that the impedance between the ablation needle and an earth pole is consistent with a real impedance of an individual measured by a treatment system, and then the model of the combination of the above two geometries is performed mesh division and computed. On the one hand, this technical solution fully considers the differences of individual impedances, which greatly improves the accuracy of temperature distribution prediction. On the other hand, it cleverly designs a simple geometric structure, which eliminates the tedious steps of skin and tissue segmentation and reconstruction, greatly simplifies the modeling and computation speed, and will help to formulate faster and more accurate clinical radio-frequency treatment plans or predict treatment results. The accuracy of the technical solution of the present application is verified by comparing the computation results of the present application with the experimental measurement result. By comparing the computation results of the present application with the temperature field prediction numerical model in the prior art, on the one hand, the computation in the present application is more accurate, and on the other hand, the computation speed in the present application is faster.

In order to make the objects, technical solutions and advantages of the present application clearer, embodiments of the present application will be further described in detail below with reference to the accompanying figures.

The first embodiment of the present invention relates to an individual impedance-based radio-frequency heating temperature field prediction method. FIG. 1 is a schematic flowchart of the individual impedance-based radio-frequency heating temperature field prediction method. The method comprises the following steps:

In step 101, creating a first region. Preferably, the first region is a large geometry based on the size of a human body, which represents a human torso tissue. Preferably, the first region is created in the body of an individual who needs radio-frequency heating, such as a human body or an animal body that needs radio-frequency heating. Optionally, a small part of the first region may not coincide with the human body, for example, it falls outside the human body, as long as the error caused is within an allowable range.

Then, into step 102, obtaining a position of an ablation needle, and with the ablation needle as a center, creating a second region in the first region. The first region and the second region in each embodiment of the present application are both three-dimensional regions, or three-dimensional spatial regions. The first region includes the second region, and preferably, the first region is much larger than the second region. Preferably, the second region is a small geometry created in the large geometry of the first region with the ablation needle as the center, representing a tissue of a target ablation region. Preferably, the second region covers an ablation range of the ablation needle.

After that, into step 103, keeping the electrical conductivity within the second region constant, and adjusting the electrical conductivity in the first region such that an impedance between the ablation needle and an earth pole is consistent with a real individual impedance actually measured by a treatment system.

Thereafter, into step 104, performing mesh division on a combination of the first region and the second region and performing coupling computation using a radio-frequency field model and a biological heat transfer model to obtain temperature field time-space information.

The shapes of the first region and the second region may be various. Preferably, the first region is an elliptic cylinder, and the second region is a cylinder. Setting the first region as an elliptic cylinder and the second region as a cylinder greatly simplifies the computation process on the premise that the computation accuracy requirements can be met. In other embodiments of the present application, the first region and the second region can also be of other shapes. For example, the shape of the first region can be a cylinder, an elliptic cylinder, a cuboid, or other geometry that simulates the shape of a human torso and is close to the size of a normal human torso. The shape of the second region can also be a cylinder, a sphere, a cuboid, or other geometry that simulates the ablation region, and its size is required to exceed the ablation range of the radio-frequency probe.

Forms of the ablation needle can be various, such as unipolar, bipolar, multipolar ablation needles, etc.

Preferably, the ablation needle is inserted vertically into the first region. Optionally, the ablation needle can be inserted into the first region at any angle.

The radio-frequency field model used in step 104 can be various. Preferably, the radio-frequency field model adopts a quasi-electrostatic field model. Optionally, the radio-frequency field model adopts a radio-frequency electric field model. Optionally, the radio-frequency field model adopts an electromagnetic wave theoretical model.

The biological heat transfer model used in step 104 can be various. Preferably, the biological heat transfer model adopts a Pennes biological heat transfer model. Optionally, the biological heat transfer model adopts a modified biological heat transfer model. Optionally, the biological heat transfer model adopts a Weinbaum JJ equation. Optionally, the biological heat transfer model adopts a heat conduction equation.

The coupling computation in step 104 is a kind of numerical computation. The implementation method of the numerical computation can also be various. Preferably, a finite element method can be used for the numerical computation. Optionally, the coupling computation can use a finite difference method. Optionally, the coupling computation can be computed by computation software.

Compared with the existing research models, the results show that on the one hand, we have greatly accelerated the modeling and computation speed by cleverly designing simple geometric structures, eliminating the tedious steps of skin and tissue segmentation and reconstruction. On the other hand, we will greatly improve the accuracy of temperature distribution prediction after considering actual impedance, which will help to formulate more accurate clinical radio-frequency treatment plans or predict treatment results.

A specific example of this implementation is described below. In this embodiment, an umbrella needle for radio-frequency ablation is taken as an example, and the difference of individual impedance is fully considered.

Figure 2:
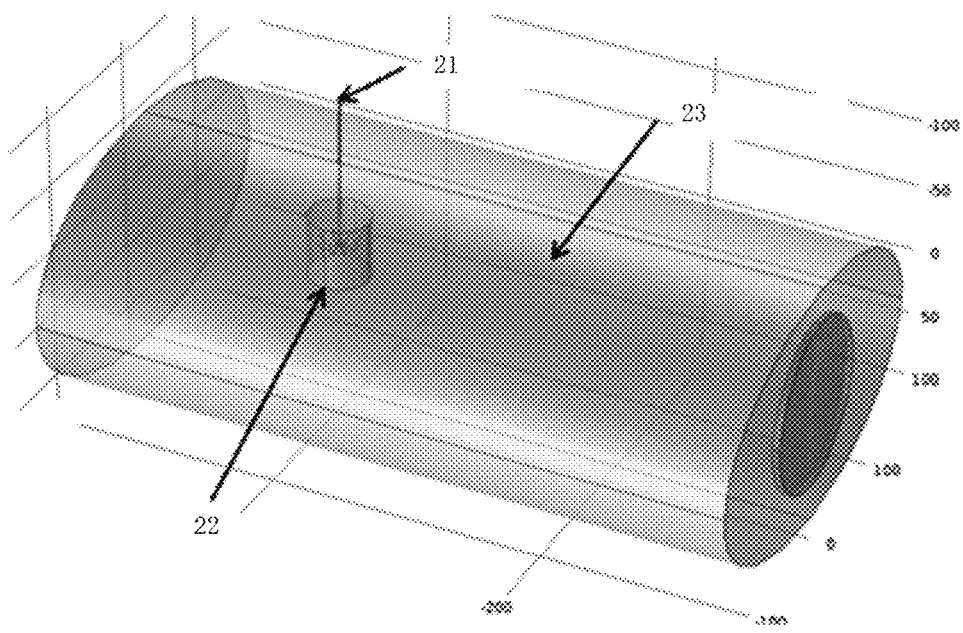
FIG. 2 is a schematic diagram of a geometric model created in an embodiment of the present application.
Figure 3:
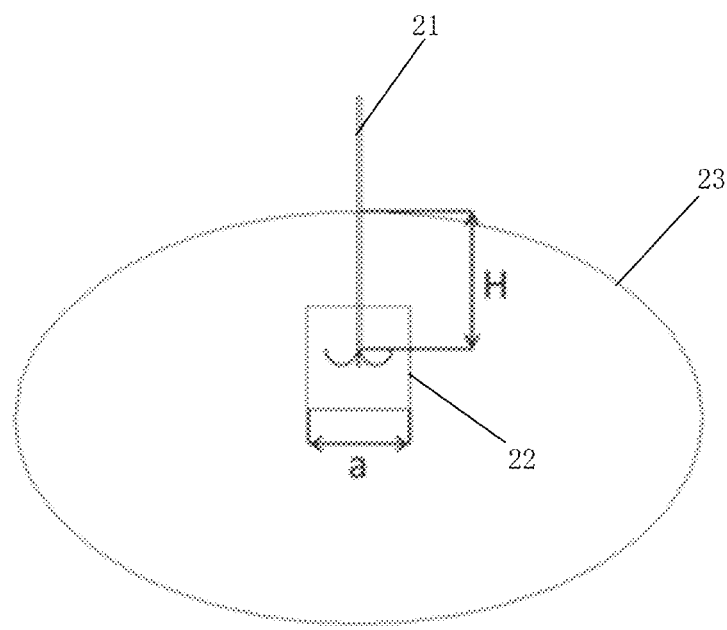
FIG. 3 is a cross-sectional view of the geometric model shown in FIG. 2 in one direction.
Figure 4:
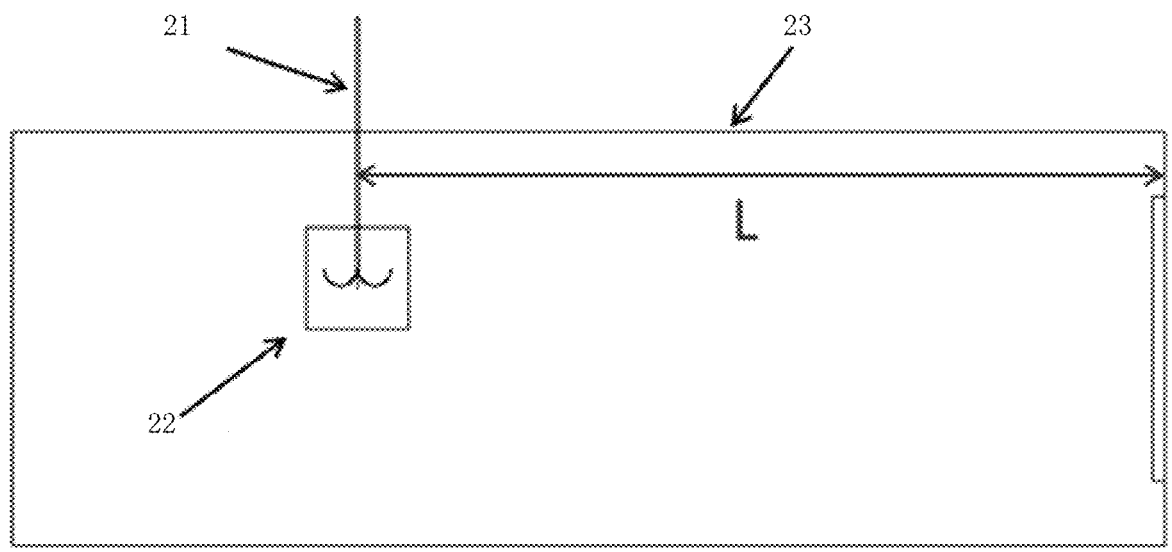
FIG. 4 is a cross-sectional view of the geometric model shown in FIG. 2 in another direction.

This embodiment comprises the following steps:

In the first step, create a large elliptical cylinder 23 (i.e. the first region) with a long axis of 30 cm, a short axis of 18 cm and a length of 45 cm in the finite element simulation software (such as Comsol), as shown in FIG. 2, FIG. 3 and FIG. 4. Set the outer large elliptical cylinder as the individual torso part.

In the second step, obtain a position of the ablation needle 21, and create a small cylinder (i.e. the second region) with the height and bottom circle diameter both of 5.5 cm in the large elliptical cylinder with the ablation needle as the center. The positive electrode of the ablation needle is placed in the center of the small cylinder, and the insertion depth H is 6 cm. The negative plate is placed on a bottom of the large elliptical cylinder, and the diameter of the negative plate is 6.2 cm. The distance L between the positive electrode and the negative electrode is 35 cm. Set the inner small cylinder as heated liver tissue, and select the ablation needle model actually used for the ablation needle.

In the third step, keep the electrical conductivity of the inner small cylinder constant, and adopt the liver conductivity used in the literature, which is set to 0.53 S/m. Adjust the electrical conductivity of the outer large elliptical cylinder, that is, individual torso part, so that the impedance between the ablation needle and an earth pole is consistent with an individual real impedance measured by a treatment system. The impedance measured in the example is 45 ohms. According to the adjustment results, the electrical conductivity of the individual torso should be set to 0.48 S/m; in the prior art model, the conductivity of the two parts of the tissue is usually set as a uniform value regardless of the impedance, namely 0.53 S/m.

Figure 5:
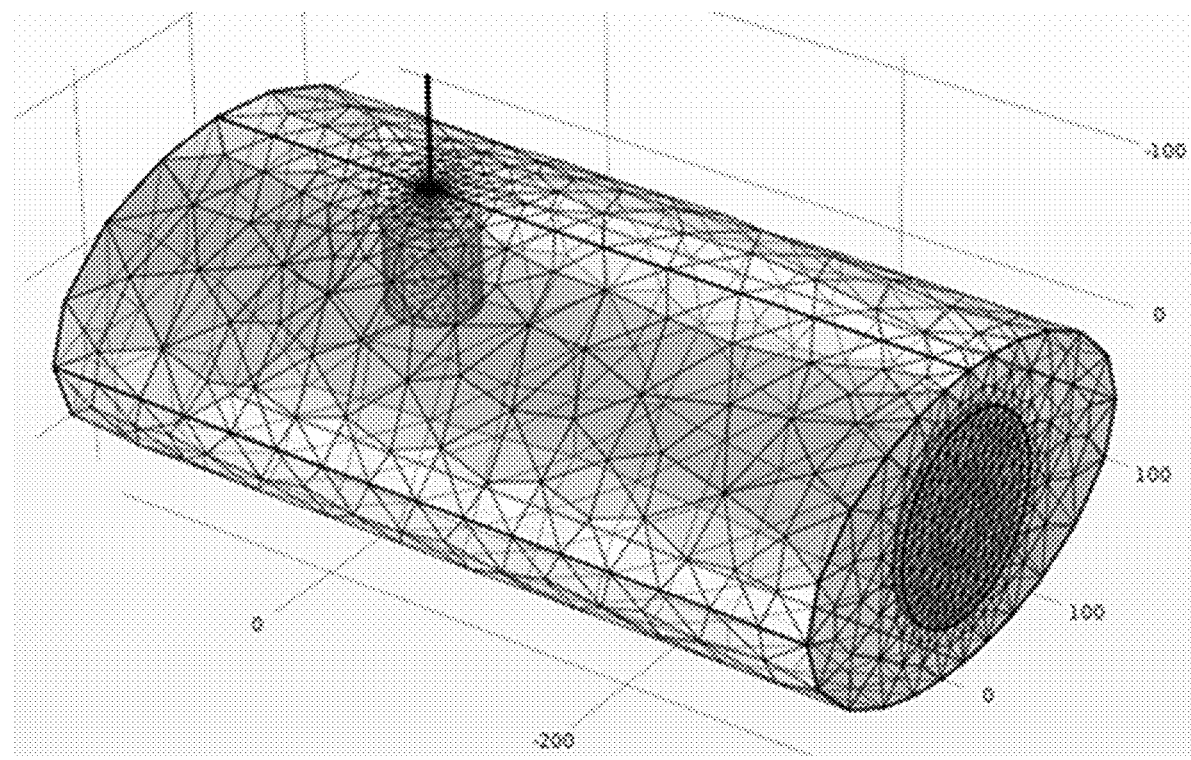
FIG. 5 is a schematic diagram of performing mesh division on the geometric model shown in FIG. 2.
Figure 6:
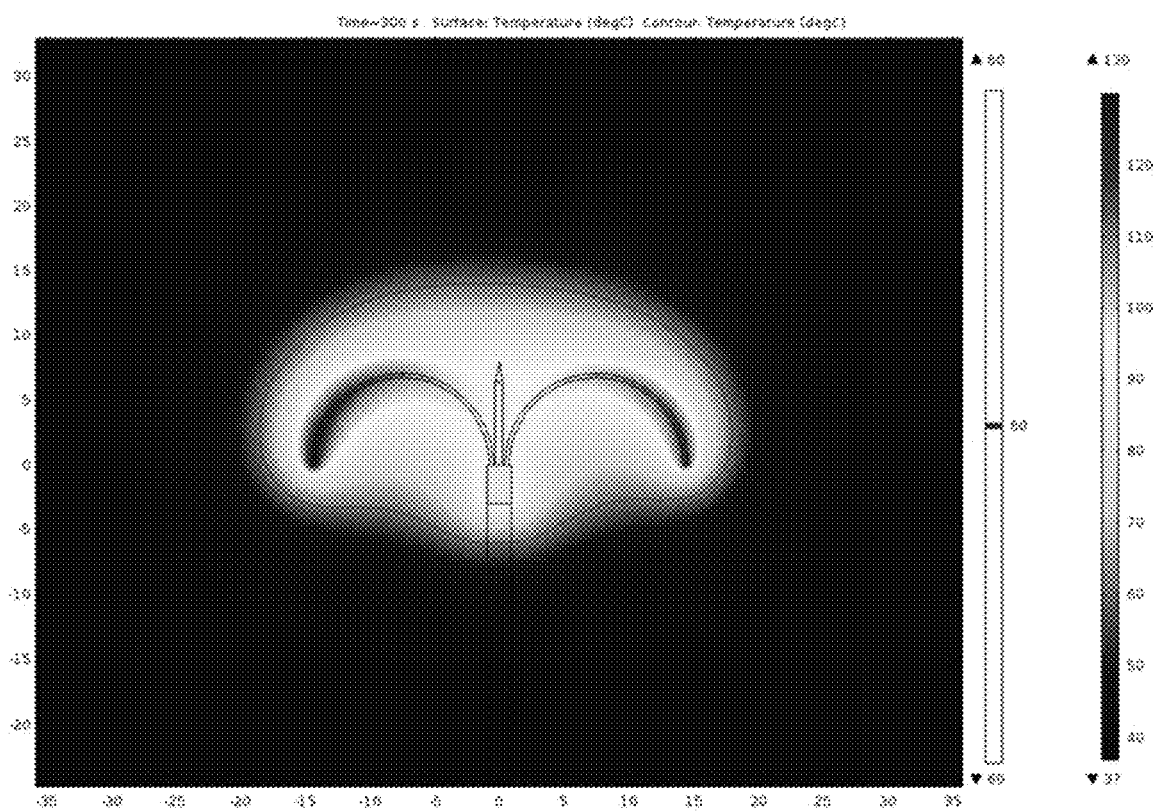
FIG. 6 is a schematic diagram of time-space information of a temperature field predicted in an embodiment of the present application.

In the fourth step, perform mesh division on a combination of the above two cylinders (as shown in FIG. 5), and refine the meshes of the ablation needle and liver tissue parts. The quasi-electrostatic field model and the Pennes biological heat transfer model are used for coupling computation to obtain the time-space information of the temperature field, as shown in FIG. 6.

The governing equation is as follows:

$$\rho c \frac{\partial T}{\partial t} = \nabla \cdot k \nabla T + \omega_b \rho_b c_b \cdot (T - T_b) + q_m + \sigma(\nabla V)^2$$

Among them, $\rho$ is the density, c is the specific heat capacity, k is the thermal conductivity, $\sigma$ the electrical conductivity, t is the time, and subscript b is the blood. In order to increase the accuracy of the model, according to literature research and experimental measurement, the thermodynamics and electrical properties of the tissue can be set as a function of temperature. $q_m$ is the heat generated by tissue metabolism, which is a temperature-related parameter. However, since the heat generated by the tissue metabolism is very small compared with the radio-frequency heating energy, $q_m$ can be ignored in most studies. T is the tissue temperature, and $T_b$ is the blood temperature, which is usually set to 37° C. $\omega_b$ is the blood perfusion rate, which can be described by the following equation:

$$\omega_b = \begin{cases} 0.0161/s & T \le 50° \text{ C.} \\ 0 & T > 50° \text{ C.} \end{cases}$$

In addition, $\omega_b$ can also be set as a function of the degree of tissue damage.

In this embodiment, the parameters used in the modeling are shown in Table 1.

TABLE 1

| structure | density (kg/m³) | specific heat capacity (J/kg · K) | thermal conductivity (W/m · K) | electrical conductivity (S/m) |
|---|---|---|---|---|
| liver tissue | 1060 | 3600 | 0.52 | 0.53 |
| individual torso | 1060 | 3600 | 0.52 | 0.365* |
| effective part of ablation needle | 6450 | 840 | 18 | 1e8 |
| insulating part of ablation needle | 70 | 1045 | 0.026 | 1e−5 |

Figure 7:
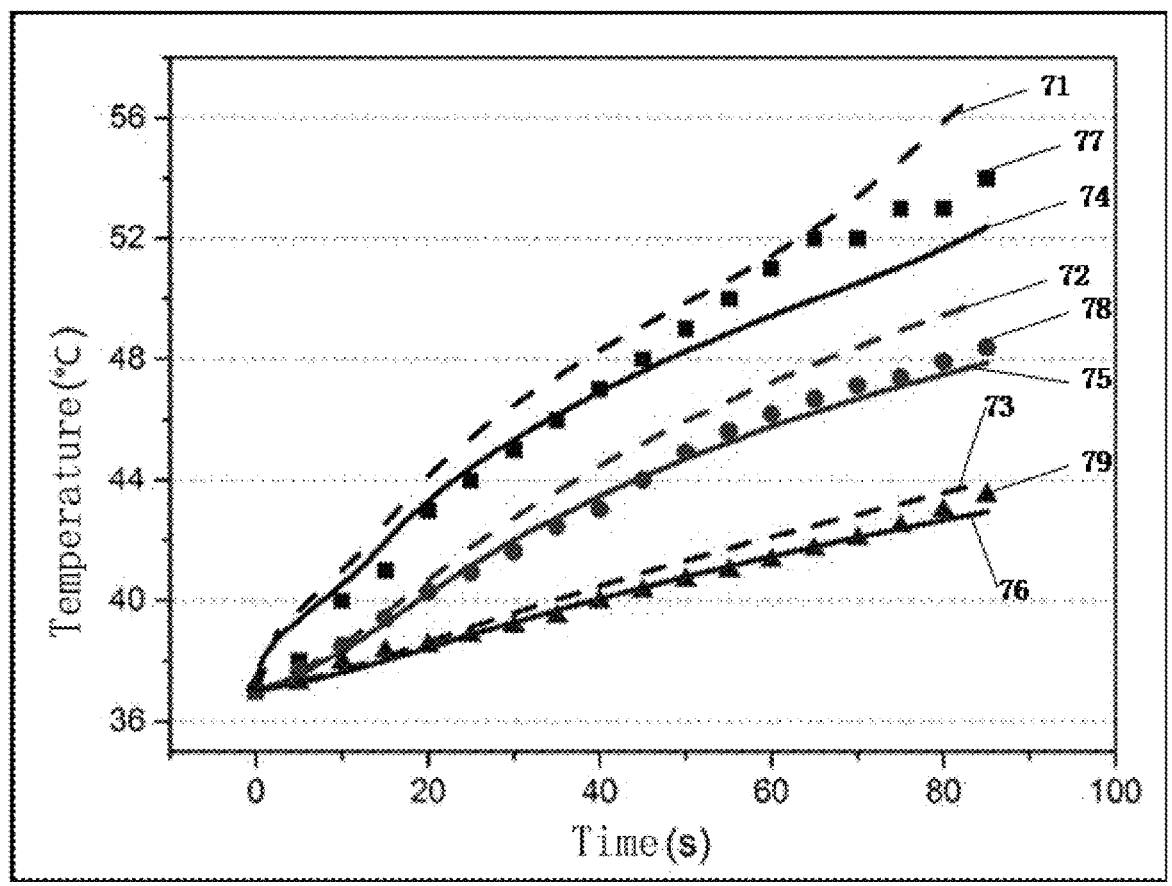
FIG. 7 is a comparison diagram of the temperature predicted by the model created in an embodiment of the present application and by the model in the prior art with the temperature measured by the experiment.
Figure 8:
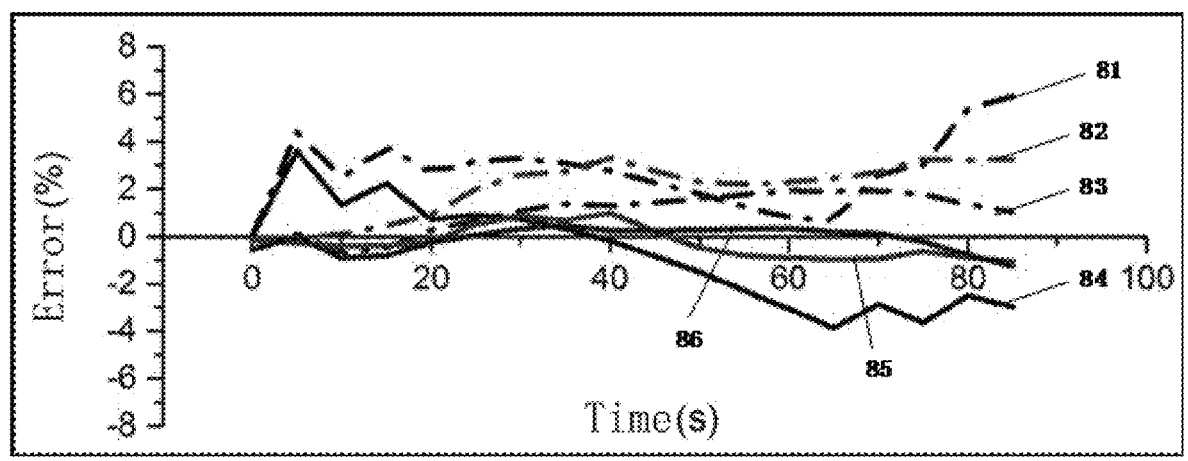
FIG. 8 is a comparison diagram of the temperature error between the temperature predicted by the model created in an embodiment of the present application and by the model in the prior art and the temperature measured by the experiment.

*The individual torso conductivity is determined by the total impedance measured To sum up, on the one hand, the present application eliminates the tedious steps of skin and tissue segmentation and reconstruction by cleverly designing simple geometric structures, which can reduce the modeling burden, speed up modeling, and reduce computation time; on the other hand, the present application fully considers the differences of individual impedances. As shown in FIGS. 7 and 8, the temperature data predicted by the present application is compared with the data measured by the experiment, and there is only 3.8% difference between the two. However, the difference between the temperature data predicted by the model in the prior art and the data measured by the experiment is 5.8%, which can prove that the temperature field prediction method proposed in the present application has achieved a better effect compared with the model in the prior art.

FIG. 7 is a comparison diagram of the temperature predicted by the model created in this embodiment and by the model in the prior art with the temperature measured in the live piglet liver radio-frequency ablation experiment. Among them, Tc is the temperature measured at the tip of the radio-frequency probe, and T1 and T2 are the temperatures measured by two thermocouples (in different positions) inserted into the live piglet body. In FIG. 7, reference numeral 71 represents the Tc curve of the model in the prior art, reference numeral 72 represents the T1 curve of the model in the prior art, reference numeral 73 represents the T2 curve of the model in the prior art, and reference numeral 74 represents the Tc curve of the model in the present application embodiment, the reference number 75 represents the T1 curve of the model in the present application embodiment, the reference number 76 represents the T2 curve of the model in the present application embodiment, the reference number 77 represents Tc curve (square data points) measured by the experiment, reference numeral 78 represents the T1 curve (circular data points) of the model in the present application embodiment, and reference numeral 79 represents the T2 curve (triangular data points) of the model in the present application embodiment. It can be seen from FIG. 7 that the curve of the present application embodiment is obviously closer to the experimental data.

FIG. 8 is a comparison diagram of the temperature error between the temperature predicted by the model created in this embodiment and by the model in the prior art and the temperature measured by the experiment. Among them, the reference number 81 represents the Tc error percentage curve of the model in the prior art, the reference number 82 represents the T1 error percentage curve of the model in the prior art, the reference number 83 represents the T2 error percentage curve of the model in the prior art, and the reference number 84 represents the Tc error percentage curve of the model in the present application embodiment, the reference numeral 85 represents the T1 error percentage curve of the model in the present application embodiment, the reference numeral 86 represents the T2 error percentage curve of the model in the present application embodiment. It can be seen from FIG. 8 that the error percentage curve of the present application embodiment is obviously more X-axis, and the error is obviously smaller.

In addition, by predicting the volume of the ablation region under other impedance and power conditions, as shown in Table 2, the model in the prior art will greatly overestimate or underestimate the ablation region if the impedance is not considered. This indicates that the present application will greatly improve the accuracy of temperature distribution prediction after considering the actual impedance, which is helpful to formulate more accurate clinical radio-frequency treatment plans or predict treatment results.

TABLE 2

Comparison results of the volume of the ablation region predicted by the model proposed in this embodiment and the model in the prior art

| conditions | model | the volume of the ablation region (m-3) |
|---|---|---|
| 55Ω/40 W/46.9 V | the model in the present application | 1.4605e−6 |
| | the model in the prior art | 2.2538e−5 |

TABLE 2-continued

Comparison results of the volume of the ablation region predicted by
the model proposed in this embodiment and the model in the prior art

| conditions | model | the volume of the ablation region (m-3) |
|---|---|---|
| 35Ω/40 W/37.4 V | the model in the present application | 2.1704e−5 |
| | the model in the prior art | 1.1458e−5 |

The second embodiment of the present invention relates to an individual impedance-based radio-frequency heating temperature field prediction system. The individual impedance-based radio-frequency heating temperature field prediction system comprises:

a first region creating unit, configured to create a first region;

a second region creating unit, configured to obtain a position of an ablation needle, and with the ablation needle as a center, create a second region in the first region;

an electrical conductivity setting unit, configured to keep the electrical conductivity within the second region constant, and adjust the electrical conductivity in the first region such that an impedance between the ablation needle and an earth pole is consistent with a real individual impedance actually measured by a treatment system; and a computation unit, configured to perform mesh division on a combination of the first region and the second region and perform coupling computation using a radio-frequency field model and a biological heat transfer model to obtain temperature field time-space information.

The first embodiment is a method embodiment corresponding to this embodiment, and this embodiment can be implemented in cooperation with the first embodiment. The relevant technical details (such as the shape and size of the first and second regions, radio-frequency field models, biological heat transfer models, numerical computation methods, etc.) mentioned in the first embodiment are still valid in this embodiment, and in order to reduce repetition, they will not be repeated here. Correspondingly, the relevant technical details mentioned in this embodiment can also be applied in the first embodiment.

It should be noted that those skilled in the art should understand that the implementation functions of the modules shown in the embodiments of the above individual impedance-based radio-frequency heating temperature field prediction system can be referred to the relevant description of the foregoing individual impedance-based radio-frequency heating temperature field prediction method to understand. The functions of each module shown in the above embodiments of the individual impedance-based radio-frequency heating temperature field prediction system can be implemented by a program (executable instructions) running on the processor, or by a specific logic circuit. If the individual impedance-based radio-frequency heating temperature field prediction system described above in the embodiments of the present application is implemented in the form of a software function module and sold or used as an independent product, it may also be stored in a computer readable storage medium. Based on this understanding, the technical solutions of the embodiments of the present application can be embodied in the form of software products in essence or part of contributions to the prior art. The computer software product is stored in a storage medium, and includes several instructions to enable a computer device (which may be a personal computer, server, or network device, and so on) to perform all or part of the methods described in the embodiments of the present application. The foregoing storage media include various media that can store program codes, such as a U disk, a mobile hard disk, a read-only memory (ROM, Read Only Memory), a magnetic disk, or an optical disk. In this way, the embodiments of the present application are not limited to any specific combination of hardware and software.

Correspondingly, the embodiments of the present application also provide a computer storage medium in which computer executable instructions are stored. When the computer executable instructions are executed by a processor, the method embodiments of the present application are implemented.

In addition, an embodiment of the present application also provides an individual impedance-based radio-frequency heating temperature field prediction system, which comprising a memory for storing computer executable instructions, and a processor; the processor is used to execute the computer executable instructions in the memory to implement the steps in the above method embodiments.

It should be noted that in the application documents of the present patent, relational terms such as first and second, and so on are only configured to distinguish one entity or operation from another entity or operation, and do not necessarily require or imply any such actual relationship or order between these entities or operations. Furthermore, the term "comprises" or "comprising" or "includes" or any other variations thereof is intended to encompass a non-exclusive inclusion, such that a process, method, item, or device that comprises a plurality of elements includes not only those elements but also other elements not clearly listed, or elements that are inherent to such a process, method, item, or device. Without more restrictions, the element defined by the phrase "comprising a/an" does not exclude that there are other identical elements in the process, method, item or device that includes the element. In the application documents of this patent, if it is mentioned that an action is performed according to an element, it means the meaning of performing the action at least according to the element, and includes two cases: the behavior is performed only on the basis of the element, and the behavior is performed based on the element and other elements. Multiple, repeatedly, various, etc., expressions include 2, twice, 2 types, and 2 or more, twice or more, and 2 types or more types.

All documents referred to in the present application are considered to be included in the disclosure of the present application as a whole, so as to serve as a basis for modification as necessary. In addition, it should be understood that various changes and modifications may be made by those skilled in the art after reading the above disclosure of the present application.

What is claimed is:

1. An individual impedance-based radio-frequency heating temperature field prediction method, comprising:
   creating a first region, wherein the first region represents torso tissue of an object to be ablated, a size of the first region corresponds to a size of a body, and the first region is an elliptic cylinder;
   obtaining a position of an ablation needle, and with the ablation needle as a center, creating a second region in the first region, wherein the second region represents tissue of a target ablation region, a size of the second region corresponds to a size of the target ablation region, the second region is a cylinder; a positive electrode of the ablation needle is placed in a center of the second region, and a negative electrode of the ablation needle is placed at a bottom of the first region;
   keeping the electrical conductivity within the second region constant, and adjusting the electrical conductivity in the first region excluding the second region such that an impedance between the ablation needle and an earth pole is consistent with a real individual impedance actually measured by a treatment system;
   performing mesh division on a combination of the first region and the second region; and
   performing coupling computation using a radio-frequency field model and a biological heat transfer model by using a finite element method for numerical computation to obtain temperature field time-space information.

2. The individual impedance-based radio-frequency heating temperature field prediction method according to claim 1, wherein the second region covers an ablation range of the ablation needle.

3. The individual impedance-based radio-frequency heating temperature field prediction method according to claim 2, wherein the ablation needle is a unipolar, or bipolar, or multipolar ablation needle.

4. The individual impedance-based radio-frequency heating temperature field prediction method according to claim 1, wherein the ablation needle is inserted vertically into the first region.

5. The individual impedance-based radio-frequency heating temperature field prediction method according to claim 1, wherein the radio-frequency field model adopts a quasi-electrostatic field model.

6. The individual impedance-based radio-frequency heating temperature field prediction method according to claim 1, wherein the biological heat transfer model adopts a Pennes biological heat transfer model.

7. An individual impedance-based radio-frequency heating temperature field prediction system, comprising:
   a memory for storing computer executable instructions; and
   a processor, configured to implement the steps in the method according to claim 1 when executing the computer executable instructions.

8. A computer readable storage medium, wherein the computer readable storage medium stores computer executable instructions, which are executed by a processor to implement the steps in the method according to claim 1.

9. The individual impedance-based radio-frequency heating temperature field prediction method according to claim 1, wherein performing mesh division includes refining meshes of the ablation needle and the second region.

10. The individual impedance-based radio-frequency heating temperature field prediction method according to claim 1, wherein the coupling computation is based on a density, a specific heat capacity, a thermal conductivity, and an electrical conductivity of each of a plurality of structures in the models.

* * * * *